United States Patent
Asah et al.

(10) Patent No.: US 6,607,523 B1
(45) Date of Patent: Aug. 19, 2003

(54) APPARATUS FOR TISSUE TREATMENT

(75) Inventors: Bjarne Asah, Taastrup (DK); Olav Balle-Petersen, Humlebaek (DK); Casper Dolleris, Vancouver (CA)

(73) Assignee: Asah Medico A/S, Hvidovre (DK)

( * ) Notice: Subject to any disclaimer, the term of this patent is extended or adjusted under 35 U.S.C. 154(b) by 0 days.

(21) Appl. No.: 09/936,328

(22) PCT Filed: Mar. 20, 2000

(86) PCT No.: PCT/DK00/00131
§ 371 (c)(1),
(2), (4) Date: Dec. 13, 2001

(87) PCT Pub. No.: WO00/56240

PCT Pub. Date: Sep. 28, 2000

Related U.S. Application Data (63) Continuation of application No. 09/272,553, filed on Mar. 19, 1999, now abandoned.

(30) Foreign Application Priority Data

Mar. 19, 1999 (DK) .................................. 1999 00389

(51) Int. Cl.[7] .............................................. A61B 18/18
(52) U.S. Cl. ................................. 606/9; 606/11; 606/18
(58) Field of Search .............................. 606/4, 5, 9–11, 606/17–18; 607/89

(56) References Cited

U.S. PATENT DOCUMENTS

| | | |
|---|---|---|
| 4,015,906 A | 4/1977 | Sharon |
| 4,387,952 A | 6/1983 | Slusher |
| 4,587,396 A | 5/1986 | Rubin |
| 4,653,495 A | 3/1987 | Nanaumi |
| 4,665,913 A | 5/1987 | L'Esperance, Jr. |
| 4,733,660 A | 3/1988 | Itzkan |
| 4,923,263 A | 5/1990 | Johnson |
| 5,048,904 A | 9/1991 | Montagu |
| 5,065,515 A | 11/1991 | Iderosa |
| 5,128,509 A | 7/1992 | Black et al. |

(List continued on next page.)

FOREIGN PATENT DOCUMENTS

| | | |
|---|---|---|
| CA | 2290760 | 6/2000 |
| DE | 3837248 | 5/1990 |
| DE | 19681641 | 10/1998 |
| EP | 075860 A2 | 6/1983 |
| EP | 699038 B1 | 11/1993 |
| EP | 724866 A1 | 8/1996 |
| EP | 8809411 A1 | 12/1998 |
| EP | 898983 A1 | 3/1999 |
| WO | 9203187 | 3/1992 |
| WO | 9308877 | 5/1993 |

(List continued on next page.)

OTHER PUBLICATIONS

NEOSCAN Model C, Operating Manuel; Medical Laser Solutions, Inc.; Sep. 1995; 15 pages.

*Primary Examiner*—Roy D. Gibson
(74) *Attorney, Agent, or Firm*—Birch, Stewart, Kolasch & Birch, LLP (57) ABSTRACT

An apparatus for tisue treatment is provided, comprising a light source for emission of a treating light beam towards a target surface and illuminating a spot on the target surface, movable deflecting means for deflection of the treating light beam, moving means for moving the deflection means, and deflecting control means being adapted to control the moving means so that the treating light beam traverses a target surface area stepwise with steps that are greater than half the diameter of the spot. Furthermore, a controlled overlap between illuminated spots may be provided, for example by user selection. The apparatus may be provided in a hand piece. The apparatus may preferably be used for removal of hairs, but also photocoagulation of veins may be obtained.

33 Claims, 9 Drawing Sheets

U.S. PATENT DOCUMENTS

| | | |
|---|---|---|
| 5,178,617 A | 1/1993 | Kuizenga et al. |
| 5,336,217 A | 8/1994 | Buys et al. |
| 5,382,770 A | 1/1995 | Black et al. |
| 5,391,165 A | 2/1995 | Fountain et al. |
| 5,397,327 A | 3/1995 | Koop et al. |
| 5,405,368 A | 4/1995 | Eckhouse |
| 5,411,502 A | 5/1995 | Zair |
| 5,474,549 A | 12/1995 | Ortiz et al. |
| 5,520,679 A | 5/1996 | Lin |
| 5,546,214 A | 8/1996 | Black et al. |
| 5,582,752 A | 12/1996 | Zair |
| 5,611,795 A | 3/1997 | Slatkine et al. |
| 5,618,285 A | 4/1997 | Zair |
| 5,620,478 A | 4/1997 | Eckhouse |
| 5,628,744 A | 5/1997 | Coleman et al. |
| 5,630,811 A | 5/1997 | Miller |
| 5,653,706 A | 8/1997 | Zavislan et al. |
| 5,735,276 A | 4/1998 | Lemelson |
| 5,735,844 A | 4/1998 | Anderson et al. |
| 5,743,902 A | 4/1998 | Trost |
| 5,786,924 A | 7/1998 | Black et al. |
| 5,798,498 A | 8/1998 | Zair |
| 5,807,386 A | 9/1998 | Slatkine et al. |
| 5,814,042 A | 9/1998 | Zair |
| 5,817,089 A | 10/1998 | Tankovich et al. |
| 5,820,625 A | 10/1998 | Izawa et al. |
| 5,827,266 A | 10/1998 | Harel et al. |
| 5,853,407 A | 12/1998 | Miller |
| 5,860,968 A | 1/1999 | Wojcik et al. |
| 5,865,828 A | 2/1999 | Jeng |
| 5,868,731 A | 2/1999 | Budnik et al. |
| 5,871,479 A | 2/1999 | Furumoto et al. |
| 5,871,480 A | 2/1999 | Tankovich |
| 5,873,875 A | 2/1999 | Altshuler |
| 5,879,346 A | 3/1999 | Waldman et al. |
| 5,885,273 A | 3/1999 | Eckhouse et al. |
| 5,906,609 A | 5/1999 | Assa et al. |
| 5,925,035 A | 7/1999 | Tankovich |
| 5,938,657 A | 8/1999 | Assa et al. |
| 5,957,915 A | 9/1999 | Trost |
| 5,971,978 A | 10/1999 | Mukai |
| 6,033,396 A * | 3/2000 | Huang et al. .................. 606/5 |
| 6,066,129 A | 5/2000 | Larson |
| 6,074,382 A | 6/2000 | Asah et al. |
| 6,110,195 A | 8/2000 | Xie et al. |
| 6,168,590 B1 | 1/2001 | Neev |
| 6,210,401 B1 * | 4/2001 | Lai ............................ 606/12 |
| 6,235,015 B1 | 5/2001 | Mead, III et al. |

FOREIGN PATENT DOCUMENTS

| | | |
|---|---|---|
| WO | 9518984 | 7/1995 |
| WO | 9622741 | 8/1996 |
| WO | 9625979 | 8/1996 |
| WO | 9716126 | 5/1997 |
| WO | 9722384 | 6/1997 |
| WO | WO 9728752 | 8/1997 |
| WO | WO 97/28752 | 8/1997 |
| WO | 9728752 | 8/1997 |
| WO | WO 98/25528 | 6/1998 |
| WO | 9825528 | 6/1998 |
| WO | 9849963 | 11/1998 |
| WO | WO 98/51235 | 11/1998 |
| WO | 9852481 | 11/1998 |
| WO | 9907438 | 2/1999 |
| WO | WO 9911324 | 3/1999 |
| WO | WO 99/11324 | 3/1999 |
| WO | 9911324 | 3/1999 |
| WO | 9917666 | 4/1999 |
| WO | 9917667 | 4/1999 |
| WO | 9917668 | 4/1999 |
| WO | WO 99/27997 | 6/1999 |
| WO | WO 99/32193 | 7/1999 |
| WO | WO 99/43264 | 9/1999 |
| WO | WO 99/60937 | 12/1999 |

* cited by examiner

APPARATUS FOR TISSUE TREATMENT

This application is the national phase under 35 U.S.C. § 371 of PCT International Application No. PCT/DK00/00131 which has an International filing date of Mar. 20, 2000, which designated the United States of America and was published in English. This application also is a continuation of U.S. application Ser. No. 09/272,553 filed Mar. 19, 1999. Further, this application claims priority under 35 U.S.C. § 119 of application number PA 1999 00389 filed in Denmark on Mar. 19, 1999.

FIELD OF THE INVENTION

The present invention relates to an apparatus for tissue treatment, such as for hair removal and for photocoagulation of veins.

BACKGROUND OF THE INVENTION

It is known to utilise laser light for tissue treatment, such as cosmetic tissue treatment, such as dermal ablation, removal of hair, photocoagulation of veins, etc.

Hair removal may be effected by directing a laser beam at a hair follicle to destroy the hair follicle and its adjacent blood vessels by the heat produced by photothermolysis.

Furthermore, coagulation of veins may be effected by directing a laser beam at the veins to coagulate the blood in the veins.

During treatment of tissue, such as an epidermal layer, hair, veins, etc, it is essential not to damage underlying or surrounding tissue. Residual heat may cause untreated cells to char and become necrotic, whereby scars may be formed. Thus, it is desirable to apply laser power only to tissue to be treated and only for a short time, to minimise transmission of conducted heat to underlying and surrounding tissue.

To some extend this has been obtained by selective photothermolysis, i.e. laser light is utilised having a wavelength that is selectively absorbed by tissue to be treated and that is not absorbed by the surrounding and healthy tissue. The selective absorption of the laser light causes selective photothermolysis in the tissue to be treated.

SUMMARY OF THE INVENTION

Light of a wavelength that is absorbed in a hair follicle and its adjacent blood vessels will be scattered in all directions when propagating from a tissue surface down to the hair follicle to be destroyed by the heat produced by photothermolysis. Therefore, it is required to illuminate a rather large spot on the tissue surface above the hair follicle (s) to be destroyed in order to increase the probability of photons being scattered in direction of the hair follicle(s). Simultaneously, the power of the illuminating light beam must be sufficient for enough heat to be generated to destroy the hair follicle and its adjacent blood vessels.

In the art this has lead to bulky hair depilators with high power lasers producing a spot size of 10 mm or more.

Throughout the present description the term spot size means the diameter of the spot in question.

It is an object of the present invention to provide an apparatus for hair removal that is adapted to automatically and accurately destroy hair follicles without damaging surrounding tissue.

It is another object of the present invention to provide an apparatus for hair removal that is adapted to remove hair from a large area of a patient.

It is a further object of the present invention to provide an apparatus for hair removal, having a handpiece that can be moved around, i.e. traversed and rotated, freely by an operator, i.e. without exerting forces acting against the movement.

According to a first aspect of the invention, the above-mentioned and other objects are fulfilled by an apparatus for tissue treatment comprising a light emitter for emission of a first light beam, movable first deflecting means for deflection of the first light beam into a treating light beam, an output for emission of the treating light beam towards a target surface and illuminating a spot on the target surface, first moving means for moving the first deflecting means, and first deflecting control means for controlling the first moving means and being adapted to control the first moving means so that the treating light beam traverses a target surface area stepwise with steps that are greater than half the diameter of the spot.

According to a second aspect of the invention, a handpiece is also provided, comprising an input connector for connection of a first beam-outlet end of a first optical fibre to the handpiece and for alignment of the first optical fibre with an axis of the handpiece so that a first light beam emitted from the first beam-outlet end is transmitted substantially along to the axis, movable first deflecting means for deflection of the first light beam into a treating light beam, an output for emission of the treating light beam towards a target surface and illuminating a spot on the target surface, first moving means for moving the first deflecting means, and first deflecting control means for controlling the first moving means and being adapted to control the first moving means so that the treating light beam traverses a target surface area stepwise with steps that are greater than half the diameter of the spot.

When the handpiece is kept in a fixed position in relation to a target surface that is illuminated by the treating light beam changing of the position of the deflecting means causes the treating light beam to traverse or scan the target surface along a curve. An area may be traversed or scanned by the treating light beam, e.g. by letting the treating light beam traverse or scan a meander like curve substantially covering the area or, by traversing or scanning the area line by line. In the present context, the type, number and shape of curves traversed by the treating light beam in order to traverse a specific area is denoted the traversing pattern or the scan pattern. The area that is scanned or traversed by the treating light beam is denoted the scan area, the treatment area or the traversed area. The scanning may be performed stepwise as further explained below.

In the art, it has hiterto been recognised that efficiency of hair removal can be increased by increasing spot size and laser power. However, it has surprisingly been found by the present inventors that a smaller spot size and a low power laser can lead to effective hair removal so that an apparatus for hair removal that is not bulky and expensive is provided according to the present invention.

According to the present invention, an apparatus for tissue treatment illuminating a spot size ranging from 1 to 9 mm, preferably from 2 to 8 mm, more preferred from 2 to 6 mm, most preferred approximately 4 mm, is provided.

It is further preferred that the output power of the diode laser is less than 250 W, preferably less than 175 W, more preferably less than 125 W, most preferred approximately 80 W.

In order to distribute energy uniformly across tissue to be treated, it is preferred to scan the tissue along a curve in steps whereby the illuminated spot is allowed to stay in a specific treating position 40–100 ms, such as 60–100 ms, preferably approximately 80 ms, followed by movement of the spot to the next treating position within a few milliseconds. Preferably, the centre to centre distance between two succeeding spot positions is less than a spot diameter, such as between half a spot diameter and a diameter of the spot, preferably such as approximately half a spot diameter, most preferred such as two thirds a spot diameter, so as to provide for a controlled overlap of the spots resulting in an effective hair removal. The thus implied overlap ensures a uniform distribution of energy across the traversed tissue area, and thus a uniform removal of hairs. It is further preferred to scan the tissue area line by line scanned successively in the same directions having a spot overlap such as mentioned above.

However, the treating light beam traverses a line to be treated a first time and a second time stepwise with a step size being substantially greater than the diameter of the spot. The centre to centre distance between two succeeding treating spot positions may be thus be larger than a spot diameter, such as 1.5 times a spot diameter, preferably such as approx. four thirds a spot diameter, and still provide effective hair removal. The scanning may be performed so that the first traversing of the treating light beam illuminates a first sequence of spots and the second traversing of the treating light beam illuminates a second sequence of spots in the same line, the distance between the first illuminated spot in the first sequence and the first illuminated spot in the second sequence being substantially equal to half the size of the steps between succeeding illuminated spots in the first sequence. The scanning may thus be performed so that after treatment of succeeding treating spots in a scan line, the line is scanned again so that the areas, the intermediate spots, not having received treatment in the first scan due to the large distance between two succeeding spots are now treated so as to obtain an overlap as mentioned above. It may then be preferred to scan the tissue area along a curve constituted by lines scanned successively in the same direction having a spot overlap such as mentioned above.

When scanning the tissue area along a curve constituted by lines scanned successively in the same or in opposite directions it is preferred that during traversing, treating spots on adjacent lines are positioned so that spot centres on one line are positioned in between spot centres on an adjacent line, whereby spot overlap as mentioned above is also obtained from one line to adjacent lines.

Alternatively, to optimise the scanning sequence the centre to centre the distance between two succeeding treating spot positions may be equal to approximately the diameter of the spot. Thus, treating spot centres are positioned as spot centres would be for hexagonal spots abutting each other.

Hair follicles and blood in blood vessels selectively absorb light energy of certain wavelengths. Thus, it is preferred to use light sources, such as lasers, generating light at wavelengths with a selective high absorption in hair follicles and preferably also in blood, preferably wavelengths larger than 190 nm, such as wavelengths in the range from 190 nm to 1900 nm, preferably from 700 nm to 900 nm, and even more preferred approximately 810 nm.

At this wavelength the absorption of the light in the hair follicles is lower than at higher wavelengths, and the energy density must therefore be higher than 50 J/cm$^2$, preferably not higher than 150 J/cm$^2$, preferably approximately 100 J/cm$^2$. The time at a specific treatment position, the spot treatment time, may vary from 30–60 ms and to several seconds. In one preferred embodiment of the invention a spot treatment time of 30–100 ms, preferably such as from 50–100 ms, such as approx. 60 ms, is used. But also longer spot treatment times, such as spot treatment times of 30 ms–3 seconds, such as 50–500 ms, or such as 100 ms–1 second, such as approx. 250 ms, approx. 500 ms, or such as approx. 1 second, may be used.

It is preferred, that the light source utilised in the present invention is a laser, such as a diode laser, such as a AlGaAs diode laser.

Furthermore, photocoagulation of veins may be obtained by traversing the target surface area stepwise. For example, a single line scan may be performed and the handpiece may be positioned so that the line scan substantially follows the vein to be coagulated. It is preferred to repeat the single line scan so that the vein is traversed by the treating light beam two or three times to ensure proper photocoagulation of the vein. The repeated treatment scans may be performed automatically.

In order to remove hairs from a tissue area, it is important that the power emitted by the light source is absorbed in the hair follicles and its adjacent blood vessels so that the hair follicles are heated to a temperature sufficient to destroy or damage the hair follicles so that the hair dies.

One way of increasing the heating of the hair follicles and the hair duct is disclosed in U.S. Pat. No. 5,925,035, ThermoLase Corporation, wherein a substance, such as a mixture of carbon particles and oil, may be applied to the tissue area to be treated. The substance may then enter the hair duct and light of a wavelength readily absorbed in the substance may illuminate the area to be treated. The power of the light source, preferably a laser, such as a Nd YAG laser, is then chosen so that the carbon particles are heated to a temperature sufficient to devitalise the tissue feeding the hair so that the hair dies, but without heating the surrounding tissue to a temperature which would otherwise induce damages in the surrounding tissue. Other substances or particles may also be applied to the tissue area to be treated, and further the hair may be stained by a dye to increase the absorption of treating light.

Alternatively, to avoid the need for application of light absorbing substances, the tissue area to be treated may be cooled during treatment. It is preferred to cool the tissue area to be treated during treatment whereby the heat is transferred through the upper dermal layers to the hair follicles, heating the hair follicles to a temperature sufficient to damage or destroy the hair follicles whereby regrowth of the hair is at least deferred, and at the same time excessive heating and corresponding damage of the surface tissue is avoided due to the applied cooling.

It is further preferred to cool the entire scan area during treatment and not just the actual spot being treated. Hereby, an effective cooling is achieved before treatment is started, during treatment and after treatment of the specific spot without the need to delay the start of treatment to allow for cooling of the specific spot area before treatment can be started and likewise without the need to await cooling of the spot after the treatment of the spot has been performed. In a preferred embodiment there is only a short delay before and after a complete scan has been performed.

It is to be understood that the application of a substance to increase the absorption of the treating light does not exclude the above-mentioned cooling of the tissue area to be treated.

The cooling of the tissue may be obtained by applying a cooling fluid, such as water, such as a gel, etc. to the surface to be treated during treatment. For example, the fluid may be applied between two plates of a material transparent to the light beams to be used during treatment. The fluid may be positioned in a substantially closed reservoir between the two plates or the reservoir may be provided with an in-let and an out-let whereby the fluid may pass through the reservoir to ensure constant cooling during treatment.

Thus, the apparatus may comprise a cooling member that is adapted to be positioned at the target area for cooling of tissue at the target area and that is at least partly transparent to the first light beam. The cooling member may comprise a frame, an upper window positioned in the frame, and a lower window positioned in the frame, the frame, the upper window, and the lower window defining a volume therebetween for receiving and holding a cooling liquid. Further, the cooling member may comprise an inlet for inputting cooling liquid to the volume and an outlet for outputting cooling liquid from the volume. The cooling member may be attached to the handpiece.

It is preferred to shape the handpiece ergonomically so that a comfortable hand grip is provided for the operator of the apparatus. For example, it is preferred to direct the light beam towards a target area at a substantially right angle to the area. The ergonomic form of the handpiece allows the operator to point the light beam at a substantially right angle to the target surface without having to bend the wrist in an uncomfortable way.

Preferably, the handpiece is light so that it is easy for the operator to hold the handpiece and bring it into any desired position in relation to target surface to be treated. The weight of a preferred handpiece according to the present invention—cables and fibres not included—is less than 300 grams, such as 290 grams, or such as 250 grams.

User interface means may be provided for selection of parameters relating to the operation of the handpiece, positioned on the housing of the handpiece.

The parameters may comprise energy density of the output light beam from the handpiece, intensity of the output light beam emitted form the handpiece, size of the target surface area to be traversed by the output light beam, shape of the target surface area to be traversed by the output light beam, etc.

The user interface means may comprise a first button, e.g. a membrane switch, for selection of a parameter type by stepping through a set of parameter types, such as the set listed above or any subset thereof.

The user interface means may further comprise a second button, e.g. a membrane switch, for selection of a parameter value of the parameter type currently selected by stepping through a corresponding set of parameter values. It is envisaged that more values may be selected for a single parameter, the sum of each value selected being the resulting parameter value. Hereby, a wide variety of parameter values is easily obtained from the user interface means.

A set of light emitting diodes may be provided for indication of the set of currently selected parameter values.

It is an important advantage of provision of the user interface at the handpiece that an operation of the handpiece is able to simultaneously select operational parameters of the handpiece and observe resulting changes in treatment effects as the operator is not forced to shift his field of view from the surface area to be treated to a user interface panel positioned somewhere else, e.g. behind the operator.

Preferably, the buttons are positioned on the housing of the handpiece so that single-handed operation is possible, preferably, with the right as well as with the left hand. The user interface means may further comprise a foot pedal. The output beam traverses a target surface area when the operator depresses the pedal. Preferably, output beam traversing is stopped immediately when the operator releases the pedal.

The deflecting means may comprise any optical component or components suitable for deflecting light of the wavelength in question, such as mirrors, prisms, grids, diffractive optical elements, such as holograms, etc, etc.

The deflecting means are preferably movably mounted for displacement of the deflecting means as a function of time, so that the light beam emitted from the handpiece may traverse a surface along a desired curve while the handpiece is kept in a fixed position. Preferably, the deflecting means are rotatably mounted, and the actual deflection of the light beam is determined by the current angular position of the deflecting means.

Moving means may be utilised to control positions of the deflecting means, such as actuators, such as piezo electric crystals, the displacement of which is controlled by applying a specific electric voltage to their electrodes, electromotors generating linear or rotational displacements, galvanometers, magnetically activated or controlled actuators, pneumatic actuators, hydraulic actuators, etc.

The positions of the deflecting means may be controlled by deflecting control means adapted to control the moving means so that the deflecting means deflect the light beam in such a way that it traverses a target surface along a desired curve.

According to a preferred embodiment of the invention, a handpiece is provided, having two mirrors that are rotatably mounted in the path of the light beam in the handpiece. The rotational axis of the mirrors may be substantially perpendicular to each other in order to obtain two dimensional deflection of the light beam.

Alternatively, the movable deflecting means may comprise one mirror that is rotatably around two aces that may be substantially perpendicular to each other.

The moving means for the mirrors may be constituted by electrometors, e.g. each mirror may be directly connected to a shaft of a corresponding motor, whereby each motor is used for angular positioning of the corresponding mirror.

In order to minimise the size of the handpiece, it is preferred to mount the motors with their respective shafts in a common plane. For example, one motor may be a linear motor, such as a linear step motor, generating linear displacements. The shaft on this motor may be connected to the mirror at a first edge of the mirror, while a second and opposite edge of the mirror is rotatably connected to the handpiece. By pushing or pulling the first edge by the linear motor, the mirror is rotated about its rotational axis. The other motor, preferably a galvanometer, may be connected to the other mirror in the conventional way described above, whereby the two mirrors may be rotated around substantially perpendicular axes.

The deflecting control means may be adapted to control the moving means so that the desired curve is a substantially straight line.

Preferably, the deflecting control means are adapted to control the moving means so that the light beam traverses a target surface area line by line.

It is an important advantage of the line by line traversing pattern that areas of any arbitrary shape, such as polygonal, such as rectangular, quadratic, triangular, etc, or circular, elliptic, etc. may be traversed line by line by appropriately controlling the starting point and stopping point of light along each line traversed.

Preferably, the first deflecting control means are adapted to control the first moving means so that the lines are traversed sequentially i.e. neighbouring lines are traversed successively. This minimises the requirement for the operator to be able to keep the handpiece steady in a desired position because when lines are traversed successively, neighbouring lines are traversed within a very short time period so that involuntary hand movements of the operator does not lead to traversing overlap i.e. involuntary hand movements can not within the very short time period during which a single line is traversed move the handpiece back to the line previously traversed which would lead to uneven treatment of the target surface.

If an interlacing traversing pattern were utilised, i.e. every second line of the target surface area is traversed and after that the remaining lines in-between are traversed, there would be sufficient time between traversing of neighbouring lines to allow involuntary movements of the handpiece to a line previously traversed leading to repeated treatment of one area that may damage tissue at that area and leaving another area without treatment.

Thus, according to a third aspect of the invention, a method is provided of traversing a light beam across an area of a tissue for depilating, comprising the steps of emitting the light beam towards the tissue area and illuminating a spot on the target area, deflecting the light beam with movable deflecting means so that the tissue is traversed by the light beam stepwise with steps that are greater than half the diameter of the spot.

The first deflecting control means may be adapted to control the first moving means so that the lines are traversed in the same direction whereby substantially the same amount of power per area is delivered uniformly across the target surface area leading to substantially the same temperature increase at any point of the target surface area after traversing. Alternatively, the first deflecting control means may be adapted to control the first moving means so that the lines are traversed in opposite directions.

When a target area is traversed line by line, it is preferred that movement of one mirror causes the light beam to traverse a line while movement of the other mirror moves the light beam to the next line. In the example above, the galvanometer preferably generates the line traversing as the galvanometer can move the mirror at a high speed, and the linear motor preferably generates the displacement of the light beam to the next line to be traversed.

In order to control positioning of curves on the target area accurately, it is preferred to position the movable deflecting means extremely accurately in the handpiece. In the preferred embodiment of the invention, this is accomplished by utilisation of printed circuit technology providing high accuracies of hole positioning of 0.05 mm. The mirrors are rotated around shafts that are mounted in printed circuit boards providing the required positioning accuracy. Further, the motors rotating the mirrors are also mounted on the printed circuit boards providing electrical connections to the motors and the mechanical support and positioning needed.

When traversing a target surface area line by line, it is preferred to traverse each line in the same direction ensuring uniform heating of cells across the target surface area. Further, it is preferred to provide light switching means for preventing emission of the light beam and light switching control means for controlling the light switching means for turning off the light beam, e.g. by switching off the light source, by inserting a light obstructing member in the light path of the beam, etc, while the light beam is moved from the end of a line having been traversed to the start of the next line to be traversed, in order to avoid repeated illumination of areas of the two lines. Further, the light switching control means may be adapted to control the light switching means for turning off the light beam while the light beam is moved from one spot to the succeeding spot.

Instead of turning the light beam off, the light beam may be moved at a speed significantly larger than the traversing speed or the parameters of the light source emitting the light beam may be controlled (e.g. by lowering the output power of the light source) so that tissue at the target area is not influenced by the light beam, during movement from the end of a line to the start of the next line. When moving the light beam from one spot to a succeeding spot it is preferred to move the light beam at high speed or to control the parameters of the light source as mentioned just above, so that tissue is not influenced when the light beam is moved over an area.

To obtain a fast treatment of large areas of similar tissue types to be treated with substantially the same treatment parameter values, it is preferred that the operator can treat a number of treatment areas without releasing the foot pedal. This facility may be provided by a repeat pattern mode when a delay is inserted after the completion of each treatment scan so as to allow the operator to move the handpiece to a new treatment position where the treatment scan is then repeated. A trained operator may only need a short delay, such as a 1 second delay, but also longer delays, up to 2 or 3 seconds, may be provided. It is preferred that the operator allow the treatment area to cool down just after treatment before the handpiece with the cooling member is removed from treatment area. This may take a few hundred milliseconds.

Typically, the intensity within the beam of a light beam as generated by the light source varies as a normal function of the distance from the centre of the beam. The optical fibre may be designed or selected to be dispersive in such a way that the intensity function of the light beam emitted from the fibre as a function of the distance to the centre of the beam is substantially rectangular, i.e. the intensity of the beam leaving the fibre decays more slowly towards the edge of the beam than the intensity of a beam as generated by the light source whereby heat is more uniformly generated in cells across a traversed line of tissue.

However, when using large spot sizes, such as the spot sizes mentioned above and used with the present invention, the intensity function of the light beam emitted from the fibre is not substantially rectangular, and furthermore due to scattering of the treating light beam at the tissue surface a spot overlap as mentioned above is necessary to obtain a uniform distribution of heat.

A light source generating visible guiding light may be provided for generating a visible guiding light beam that is used to assist the operator by indicating areas towards which the treating light is directed during traversing. For example, the input connector of the handpiece may be further adapted to connect a second beam-outlet end of a second optical fibre for transmission of a visible guiding light beam to the handpiece. The second optical fibre is aligned in the connector along the desired path of the visible light beam. The handpiece may further comprise movable second deflecting means for deflection of the visible guiding light beam in such a way that the treating light beam and the visible guiding light beams emitted from the output of the handpiece illuminate substantially the same area of a target surface.

Preferably, the treating light and the guiding light are transmitted through the same optical fibre and via the same optics so that the spots illuminated by treating light and guiding light, respectively, are substantially identical.

In order to assist the operator of the apparatus in keeping a constant distance from the output of the handpiece to the surface of the tissue to be ablated, the handpiece may comprise a distance member connected to the handpiece at the output with fastening means.

As the distance member will touch the patient, it is desirable to insert a new, disinfected member before treatment of a new patient and thus, it is preferred that the fastening means comprises a magnet so that a used distance member can easily be disconnected from the handpiece, e.g. for autoclaving, and so that a new member can easily be connected to the handpiece.

The handpiece according to the present invention may further comprise a processor for control of the handpiece and comprising one or more control means, such as deflecting control means, light switching control means, means for controlling the light intensity control means, etc. The processor may further be connected to the user interface means and may be adapted to control the functions of the handpiece in accordance with the user interface selections.

Thus, the processor may be adapted to control energy density received by the target surface when traversed by the treating light beam.

The processor may comprise a memory, such as an EEPROM, a flash EEPROM, for storing of different parameters of traversing patterns, such as target surface area size, traversing duration, energy density, etc.

The handpiece may further be provided with a computer interface facilitating reception of traversing pattern parameters generated in a computer and transmitted to the handpiece for storage in the memory. The user interface may be utilised for selection of a specific traversing pattern from the set of patterns stored in the memory as previously described. The computer may be any programmable electronic device capable of storing, retrieving and processing data, such as a PC.

It is an important advantage of provision of a processor in the handpiece that signal lines between the handpiece and an external device controlling the handpiece are not needed. This reduces weight of the handpiece with cables connected. Further, electrical noise on control lines is minimised because of reduced lengths of the lines. Still further, control speed is increased as capacitance of a short line is small.

Various traversing patterns may be created on a PC and be downloaded to the memory of the handpiece. The patterns may stored in the form of a table of parameters defining number of lines, length of lines, distance between lines, start and end points of fade-in and fade-out of each line, points of turn on and turn off of the traversing light beam, etc of each traversing pattern stored.

A traversing pattern box may be provided, containing a processor, a memory and interface means for storage of traversing patterns generated, e.g. on a PC and transmitted to the box through the interface means for storage in the memory. The interface means of the box and the computer interface of a handpiece may be interconnected and the various traversing patterns stored in the box may be transferred to the memory of the handpiece whereby traversing patterns created at a single PC may be distributed to a plurality of handpieces that may be situated remotely from the PC.

BRIEF DESCRIPTION OF THE DRAWINGS

In the following, a preferred embodiment of a cosmetic tissue treatment apparatus will be described with reference to the drawings, wherein.

DETAILED DESCRIPTION OF THE DRAWINGS

Figure 1:
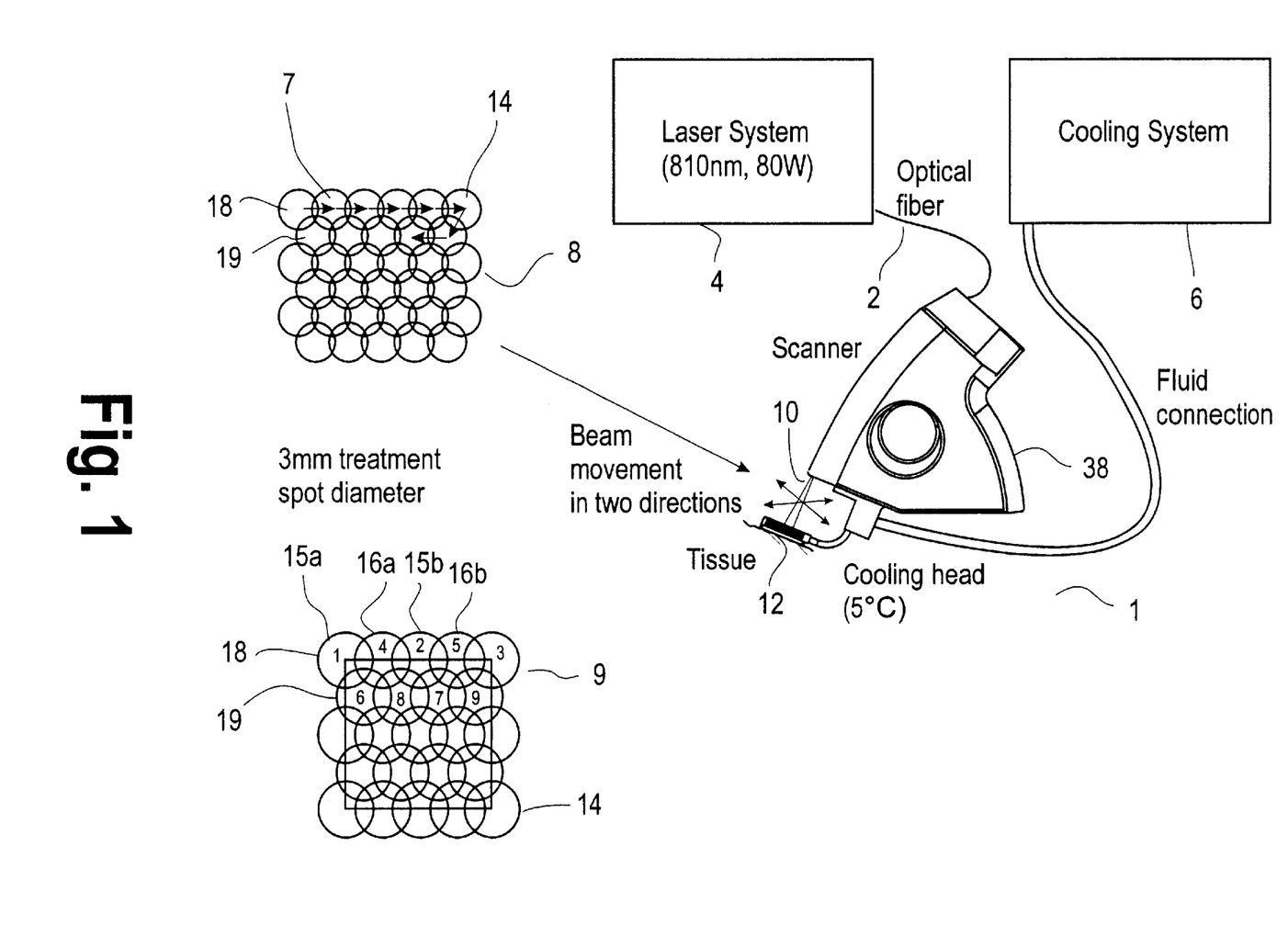
FIG. 1 shows schematically an apparatus for tissue treatment and scan patterns according to the present invention.

FIG. 1 shows an apparatus for tissue treatment 1 according to the present invention. The depilator 1 comprises a handpiece 38 comprising an input connector for connection of a first beam-outlet end of an optical fibre 2 to the handpiece 38 and for alignment of the optical fibre 2 with an axis of the handpiece 38 so that a treating light beam emitted from the first beam-outlet end is transmitted substantially along the axis. As further explained below, the handpiece 38 also comprises movable first deflecting means for deflection of the first light beam into a treating light beam, an output 10 for emission of the treating light beam towards a target surface 12 and illuminating a spot 14 on the target surface 12, first moving means for moving the first deflecting means, and first deflecting control means for controlling the first moving means and being adapted to control the first moving means so that the treating light beam traverses a target surface area 12 stepwise with steps that are grater than half the diameter of the spot 14.

In the present example, the spot size is approximately 3.7 mm, and the output power of the AlGaAs laser diode 4 is approximately 82 W.

In order to distribute energy uniformly across tissue to be treated, it is preferred to scan the tissue line by line in steps whereby the illuminated spot is allowed to stay in a specific treating position 50–100 ms, preferably approximately 50 ms, followed by movement of the spot to the next treating position within a few milliseconds. Two different scan patterns are shown in FIG. 1. Preferably, the scan pattern 9 is applied, wherein the treating light beam traverses a line to be treated a first time and a second time stepwise with a step size being substantially greater than the diameter of the spot. The scanning is performed so that the first traversing of the treating light beam illuminates a first sequence of spots 15a, 15b, etc and the second traversing of the treating light beam illuminates a second sequence of spots 16a, 16b, etc in the same line, the distance between the first illuminated spot 15a in the first sequence and the first illuminated spot 16a in the second sequence being substantially equal to half the size of the steps between succeeding illuminated spots in the first sequence. That is, the distance between two succeeding treating spot positions 14, for example the distance between treating spots 15a and 15b, is equal to approx. four thirds the diameter of the treating spots 14. After treatment of line 18, the intermediate spots 16a and 16b are treated so that the light energy is distributed uniformly across the traversed tissue area 8 with a predetermined spot overlap, i.e. the resulting centre to centre distance between spots 15a and 16a is approx. two thirds of the diameter of the spots 14. Preferably, the spot overlap is approx. 24%. Thus, having a spot size of 3.7 mm, the centre to centre distance between adjacent spots 15a and 16a is then approx. 2.5 mm, and the centre to centre distance between two succeeding treating spots 15a and 15b is approx. 5 mm. During traversing, treating spots 14 on adjacent lines 18, 19 are positioned so that spot centres on one line 18 are positioned in between spot centres on an adjacent line 19, whereby spot overlap as mentioned above is also obtained from one line to adjacent lines.

Investigations has shown that only part of the spot size is active when the tissue area is treated. This is partly because the intensity profile is always decaying towards the edges and is not a rectangular profile, and further as the intensity is lower towards the edges of the profile, relatively more light will be scattered on the tissue surface. As a rule of thumb, it is found that having a spot diameter of 3.7 mm only the centre 2.5 mm part of the spot is active when treating tissue.

An alternative span pattern 8 may also be applied, wherein a the tissue is scanned along a meander curve 7 in steps whereby the illuminated spot is allowed to stay in a specific treating position 60–100 ms, preferably approximately 80 ms, followed by movement of the spot to the next treating position within a few milliseconds. Using this scan pattern, the distance between two succeeding treatment spots is approx. 3.1 mm, i.e. approx. 84% of the spot diameter, whereby light energy is distributed across the traversed tissue area 8 with a predetermined overlap. During traversing, treating spots 14 on adjacent lines 18, 19 are positioned so that spot centres on one line 18 are positioned in between spot centres on an adjacent line 19, whereby spot overlap as mentioned above is also obtained from one line to adjacent lines.

The light beam from a diode laser 4 is coupled into the optical fibre 2 at one end of the fibre 2 positioned at one end of the cable 1. At the same end of the optical fibre 2, a guiding light beams from a diode laser is coupled into the optical fibre 2. The treating and guiding light beams are transmitted in the optical fibre from the inlet end to the outlet end, which is connected to the handpiece 38.

Figure 2:
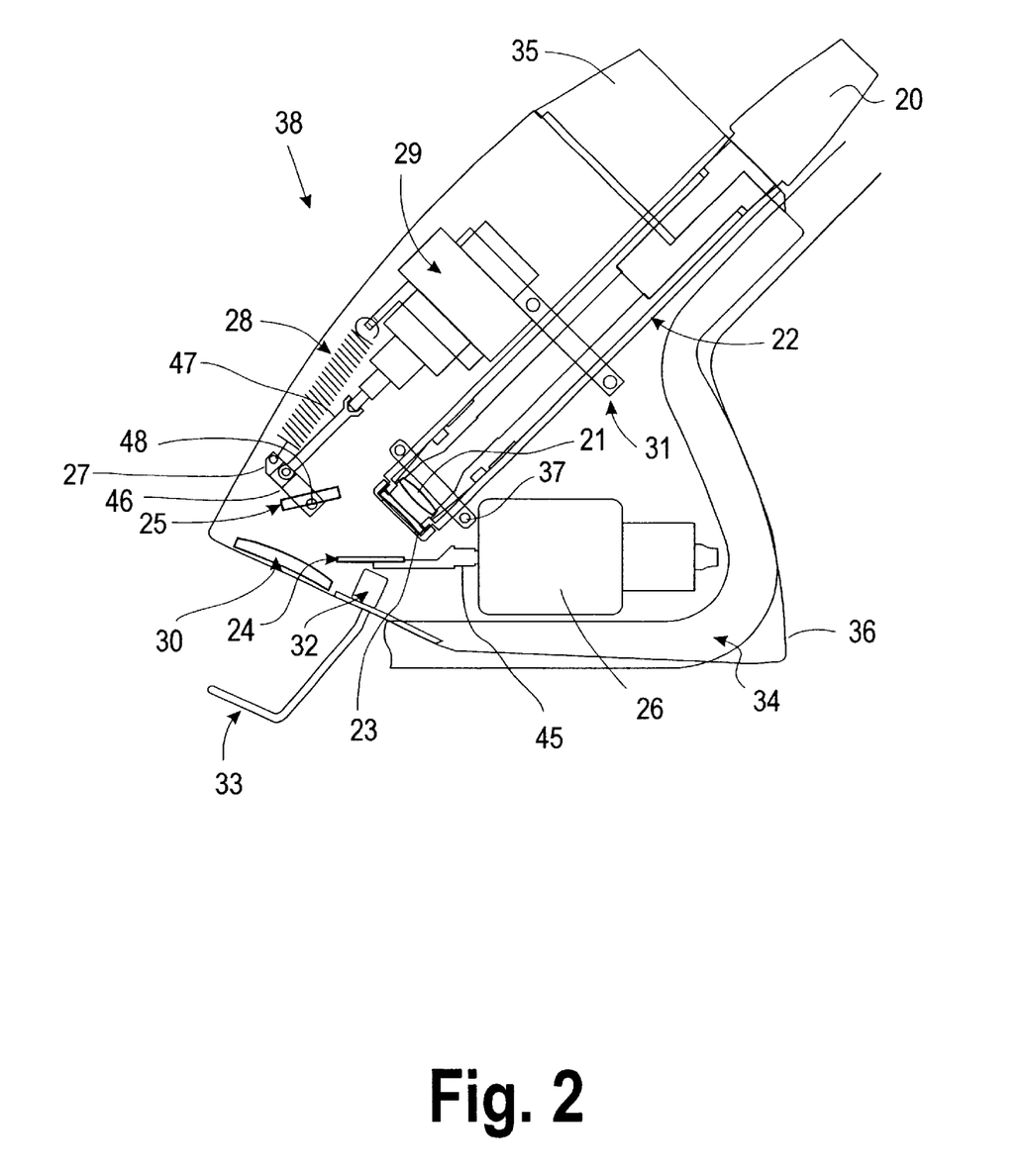
FIG. 2 shows a cross section of a handpiece according to the present invention.

FIG. 2 shows a handpiece 38 according to the present invention. The optical fibre 2 (not shown in FIG. 2) is connected to the handpiece 38 at a fibre inlet part 20, and guided through a tube 22 which is held in place in the handpiece 38 by the holding means 31 and 37. The fibre inlet part 20 also serves as a cable protecting sleeve. The light beams transmitted in the optical fibre 2 are radiated from the outlet ends of the fibre 2 through a lens system 39—shown in greater detail in FIG. 3—to an object, e.g. a human tissue surface. The outlet end of the fibre 2 is positioned at the holding means 37 at a distance appropriate for the focusing lens 21 to focus the light from the fibre 2 on the object.

Figure 3:
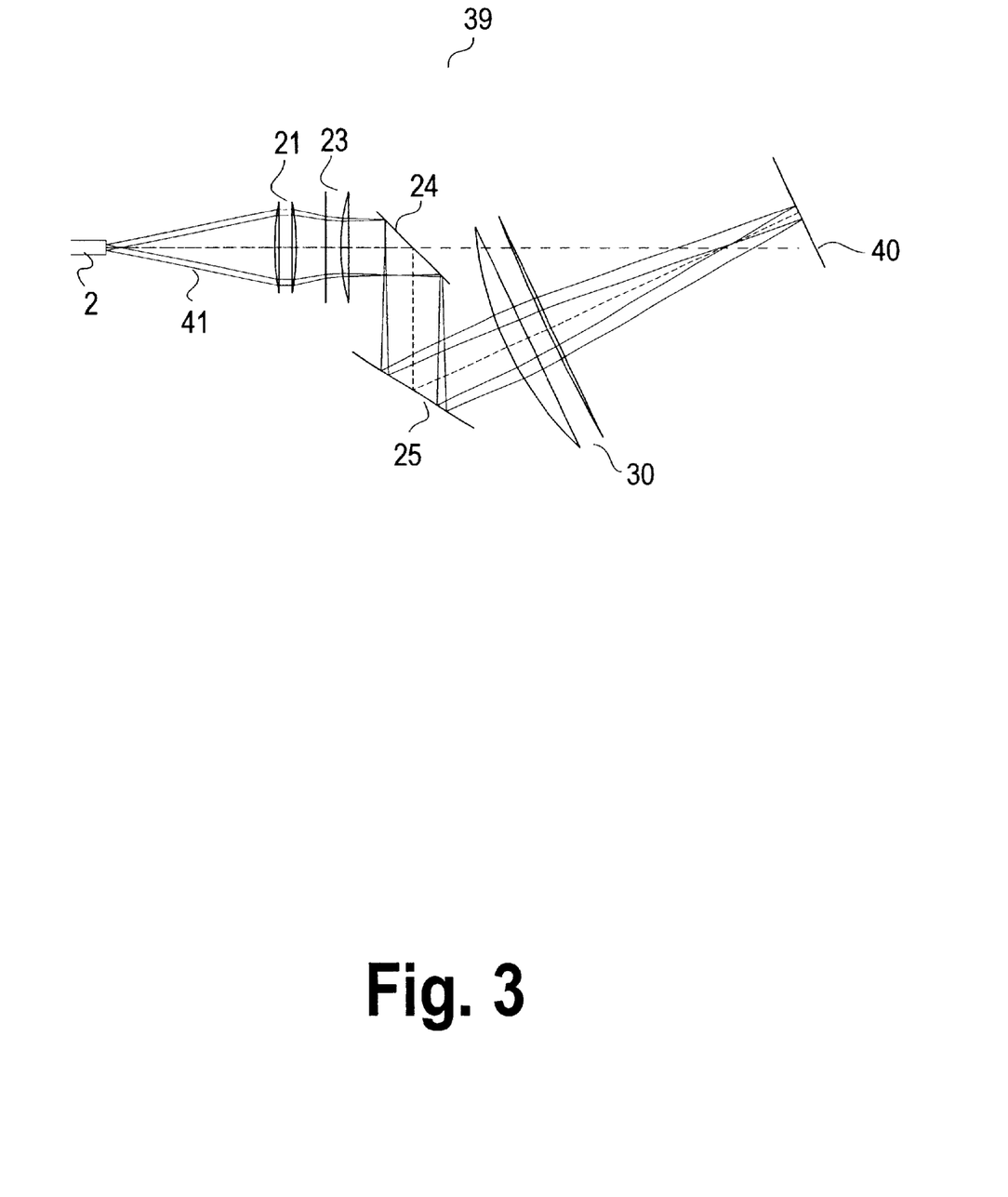
FIG. 3 shows the lens system of the handpiece shown in FIG. 2 in greater detail.

In FIG. 3, the lens system 39 is shown in greater detail. The light beams radiated from the outlet end of the fibre 2 are focused by the first focusing lens 21 and collimated by the collimating lens 23. The collimated light beam are transmitted from the collimating lens 23 via a first mirror 24 and a second mirror 25 to a second focusing lens 30 which focuses the light beams on the object 40, which e.g. can be the facial tissue of a human being. The distance between the focusing lens 30 and the focus plane at the object 40 is preferably approx. 28 mm.

The movable first deflecting means also constitute the second movable deflecting means and comprise the first mirror 24 that is mounted on the first moving means that also constitute the second moving means and comprise a galvanometer 26 with an indicator 45 and positioned in the handpiece 38 of the handpiece according to the invention. When an electric current is driven through the coil of the galvanometer 26, the magnetic field generated by the current will make the indicator 45 rotate around a longitudinal axis of the indicator 45. The first mirror 24 will thereby be rotated, and the treating light beam will be deflected at an angle twice the angle rotated by the mirror 24 in relation to the first light beam. The positioning resolution of the galvanometer 26 is limited by the electronic deflecting control means controlling the galvanometer 26 to 255 positions.

The movable first deflecting means also comprise the second mirror 25, and is mounted on an arm 46 actuated by a linear actuator 29 comprised by the first moving means. When the linear actuator 29 activates the actuator arm 47, the arm 46, and thereby the second mirror 25, is rotated around the shaft 48. A spring 28 is connected to one end of the arm 46 and to a non-moving part of the linear actuator 29 in the other end so as to neutralise wobble that may be present in the shaft 48. When the second mirror 25 is rotated around the shaft 48, the light incident on the second mirror 25 is deflected in an angle twice the angle rotated by the mirror 25. The linear actuator 29 may be controlled by applying a sequence of pulses across the terminals (not shown) of the actuator 29. The positioning resolution of the linear actuator is discrete and limited to a maximum number of steps of approx. 200.

The optics of the apparatus limits the possible scan area to approx. 23*23 mm, corresponding to an angular displacement of the mirror 24 of approx. ±8° and an angular displacement of the mirror 25 of approx. ±5°, even though the maximum movement of the mirror 24 is approx. ±11° and the maximum movement of the mirror 25 is approx. ±10°. The extra possible movement which is not used during scanning is used during start-up of the system to ensure accurate and reliable speed before the treatment scan is started.

By controlling the current to the coil of the galvanometer 26 and the pulse sequence applied across the terminals of the linear actuator 29, the direction of light beams sent through the focusing lens 30 towards the object 40 can be controlled. It is thus possible to create different kinds of scan patterns of the light beam, such as rectangular, circular or line scan patterns.

The optics and electronics of the handpiece 38 are protected by a plastic housing 36 provided in an ergonomical shape. An air tube 34 may be positioned on the handpiece 38 for providing suction of air from in front of the optics of the handpiece 38 in order to absorb any material ablated from the tissue of the object being treated with the apparatus of the present invention.

Because of the importance of keeping the treating beam focal point on the tissue surface, the presently preferred embodiment of the handpiece 38 further comprises a magnetic distance member 33 connected to the handpiece 38 with a magnet. As the distance member 33 is magnetic, it is easy to connect to and disconnect from the handpiece 38.

Figure 4:
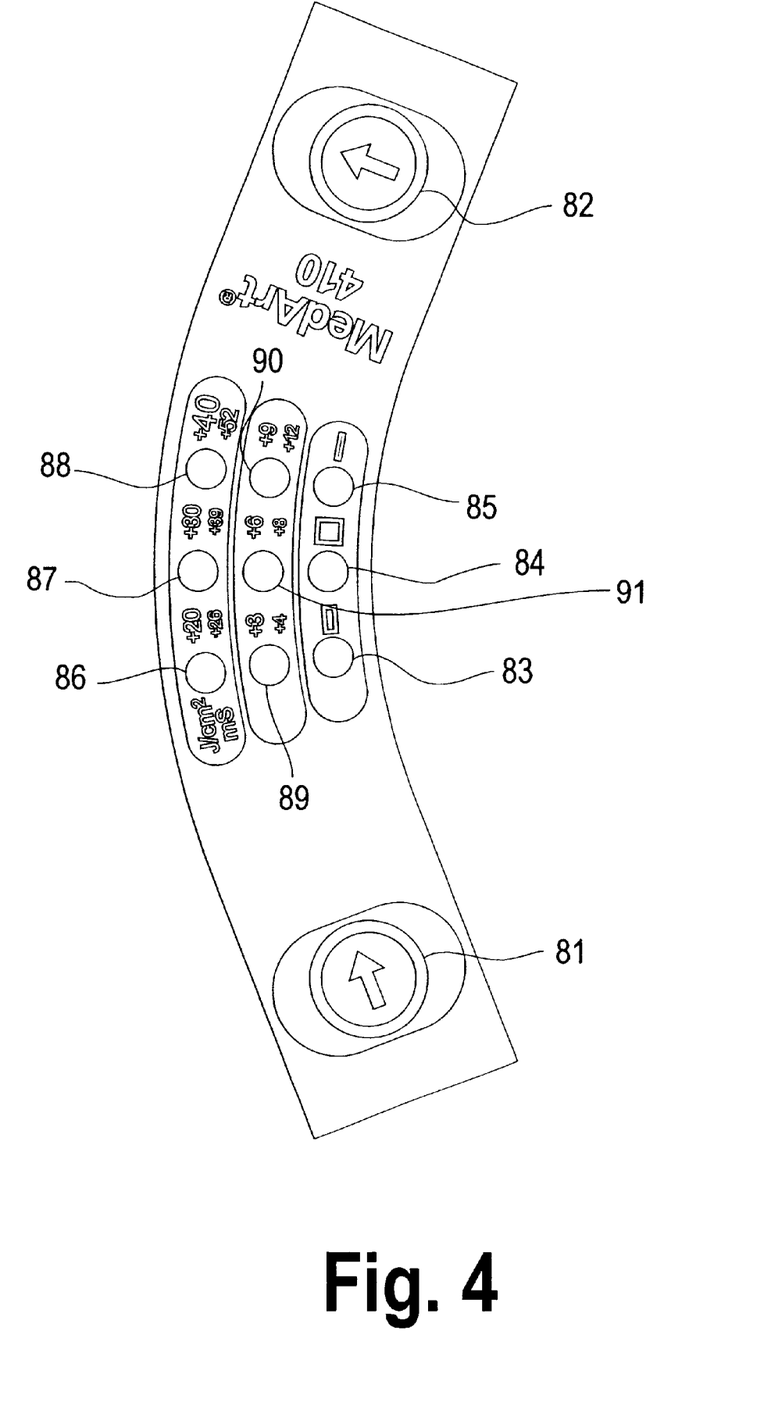
FIG. 4 shows an unfolded view of the user interface means provided at the handpiece.

In FIG. 4, the user interface means of the handpiece is shown unfolded. The user interface means comprise two push buttons 81, 82 and nine light emitting diodes arranged in three rows, each row comprising three diodes.

Each row is used to indicate selection of a parameter value of a corresponding parameter type.

The row comprising diodes 83, 84, and 85 indicates selection of shape of the scan pattern. Diode 83 is turned on when a rectangular scan pattern is selected, diode 84 is turned on when a quadratic or square scan pattern is selected and diode 85 is turned on when a line scan pattern is selected.

Figure 5A:
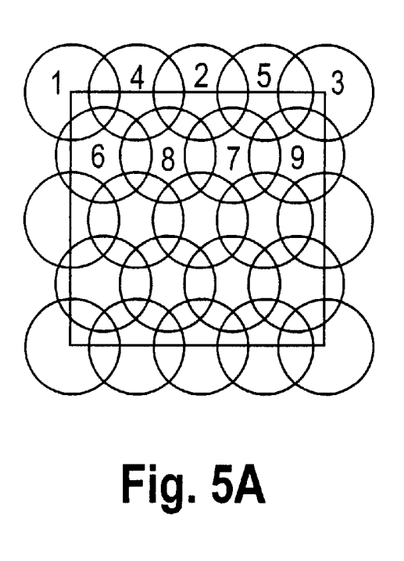
FIGS. 5a–c show three different scan patterns.
Figure 5B:
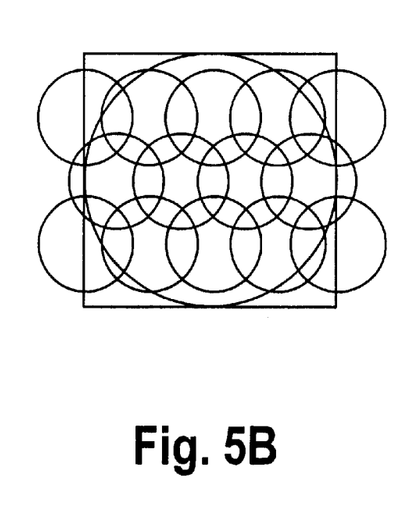
Figure 5C:
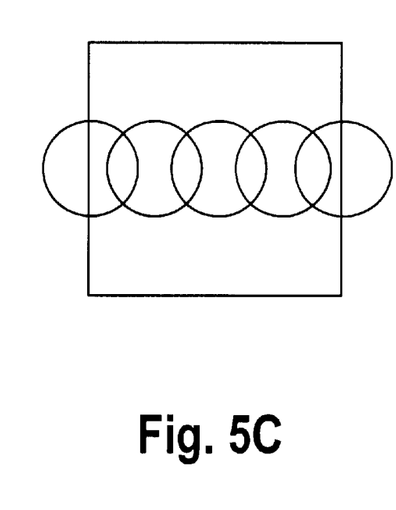

In FIGS. 5a–c, three different scan patterns are shown according to the preferred embodiment of the invention described in these examples. The distance from the handpiece to the scan area is 28 mm and the spot size is 3.7 mm. The full scan area is 10 mm×10 mm plus 3.7 mm spot size, thus the effective scan area is 13.7 mm×13.7 mm (1,877 cm$^2$). If the square scan is selected there will be 23 treating spots 14, distributed in 5 lines in the scan area as seen in FIG. 5a, if the scan is rectangular there will be 14 treating spots, distributed in three lines in the scan area as seen in FIG. 5b, and if the line scan is selected there will be 5 treating spots in one line in the scan area as seen in FIG. 5c.

In another preferred embodiment the distance from the handpiece to the scan area is 58 mm and the spot size is 4 mm. The scan area is then 14,5 mm×16 mm+4 mm spot size, thus the effective scan area is 18,5 mm×20 mm (3,7 cm$^2$). If the square scan is selected there is 39 treating spots, distributed in 7 lines, in the scan area, if the scan is rectangular there is 17 treating spots, distributed in three lines, in the scan area, and if the line scan is selected there is 5 treating spots in one line in the scan area.

Referring to FIG. 4, the row comprising diodes 86, 87, and 88 indicates energy density or fluence. One or more diodes may be turned on at the same time indicating that the values of the lit diodes are to be added to provide the output fluence. Furthermore, as the laser power is constant the selection of the energy density implies a selection of the treatment time. Thus, diode 86 is turned on when 20 J/cm$^2$ and a treatment time of 26 ms is selected, diode 87 is turned on when 30 J/cm$^2$ and a treatment time of 39 ms is selected, and diode 88 is turned on when 40 J/cm$^2$ and a treatment time of 52 ms is selected, and further diodes 86 and 87 are turned on when 50 J/cm$^2$ and a treatment time of 65 ms is selected, and diodes 86, 87 and 88 are turned on when 90 J/cm$^2$ and a treatment time of 117 ms is selected, etc.

Furthermore, the row comprising diodes 89, 90 and 91 indicates additional energy density or fluence, so that the value(s) of the lit diode(s) in this row are to be added to the value(s) of any of the lit diodes 86, 87 and 88. If diode 86 is turned on and further diode 90 is turned on a fluence of 26 J/cm$^2$ (20+6 J/cm$^2$) and a treatment time of 34 ms (26+8 ms) is selected, etc. It is thus possible to select any fluence from 20 J/cm$^2$ to 108 J/cm$^2$ in steps of 3 J/cm$^2$ with the treatment times ranging from 26 ms to 141 ms.

For example, when scanning a square scan pattern with a laser output power at 82 W and a selected fluence of 20 J/cm$^2$ the time to complete a scan, a full scan, will be 1.2 seconds, and with a selected fluence of 108 J/cm$^2$ the time to complete a scan will be 5.3 seconds.

Depression of the push bottom 82 causes one of the light diodes to start flashing in one row indicating that parameter values of the type corresponding to that row can be selected. By depressing push button 82 once more, a light diode in another row will start flashing and thus, by repeatedly depressing push button 82, parameter values of each type indicated by the user interface means may be selected.

In the row in which a light diode is flashing, the desired parameter value may be selected by depressing the push bottom 81 until the diode indicating selection of the desired parameter value is flashing.

Thus, selection of scan area parameter values of the handpiece and energy densities of the light beam may be done immediately prior to scanning of the treatment area. Selection is very simple and does not require utilisation of an external computer for programming of desired scan patterns.

The different scan pattern parameter values are stored in the memory of the handpiece. This provides an easy to learn and understand user interface requiring a minimum of teaching of the operator. Furthermore, the weight of the cables and thereby of the handpiece is reduced because there is no need for cables connecting the handpiece to an external controller. Further, by storing scan pattern parameters in the memory of the handpiece, costs for an expensive programming device is avoided. Other scan patterns than the ones described above may be downloaded to the memory of the handpiece through its computer interface. When the desired scan patterns have been downloaded, the computer interface can be disconnected from the scan pattern parameter value source and the handpiece will be ready for use.

All functions of the handpiece is controlled by the processor. The processor is interfaced with the laser unit, the light emitting diodes and the two push buttons of the user interface means.

Other interface means positioned at the handpiece may be provided where other parameters may be chosen. For example, other treatment area shapes and treatment area sizes may be chosen, and furthermore, instead of choosing specific fluence values and corresponding treatment times specific laser programs may be chosen. The light diodes 86–91 may thus indicate selection of different laser programs, wherein each laser program contains a specific profile comprising for example wavelength, output power, energy density, treatment time or active time, spot treatment time, duty cycle, pulse width, inter pulse delay, etc, each program being designed to treatment of specific tissue profiles. Hereby, the operator may select a known program having optimal settings for the specific tissue type to be treated. The information comprised in each program may be displayed on a display, such as a display provided at the laser, an external display, a display positioned on the handpiece, etc. The program files may be stored in the memory of the handpiece or alternatively they may be stored in a memory positioned in the laser unit.

Figure 6:
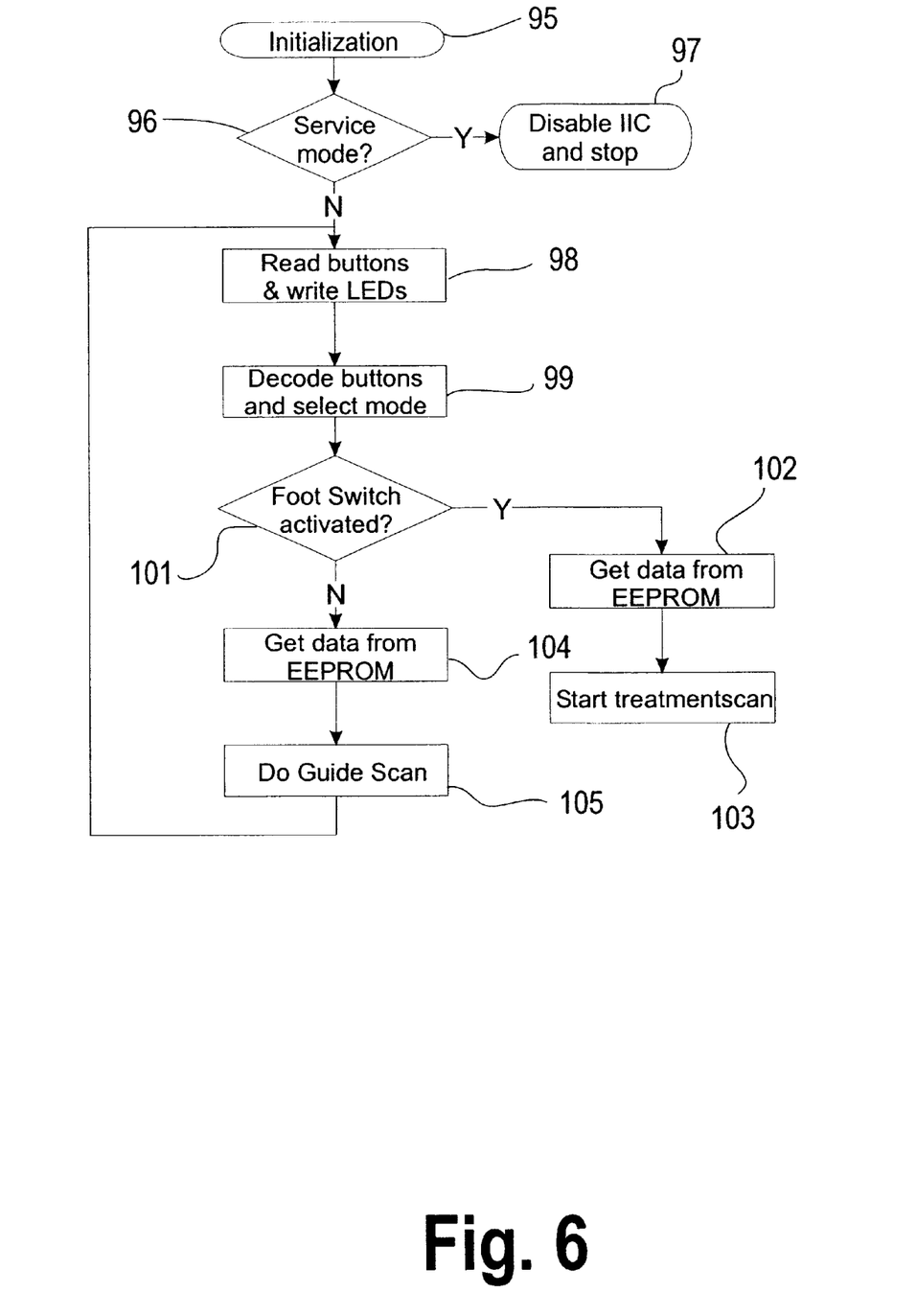
FIG. 6 shows a flow chart of the software controlling the scan parameters.

In FIG. 6 a flow chart illustrates processor operation before the treatment scan is started.

Processor operation starts in step 95 where the processor is initialised. Hereafter in step 96, the processor checks if the handpiece is in a serve mode. If so, the bus IIC, which reads and writes the outputs from the two interface integrated circuits IC11 and IC12 is disabled in step 97 as described further in the next section. If not, in step 98 activation of the push buttons of the user interface means are detected and the light emitting diodes are turned on and off accordingly as previously described. In step 99, the parameter value selections are recorded and the corresponding scan pattern and fluence settings are selected. In step 101, the processor checks if the foot pedal is depressed or activated. If so, in step 102 the processor gets data from the memory of the handpiece, the EEPROM, and starts the treatment scan in step 103. If not, the processor gets data from the EEPROM in step 104 and perform a guide scan in step 105, i.e. the visible light beam, traverses the circumference of the scan pattern or a part thereof as previously described. Hereafter the process is repeated from step 98. The visible light beam is for example a light beam with a wavelength of 635 nm and a 5 mW output power.

The processor may be set in repeat mode so that the operator can treat a number of treatment areas without releasing the foot pedal. A delay is then inserted after the accomplishment of each treatment scan so as to allow the operator to move the handpiece to a new treatment position. A trained operator may only need a short delay such as a 1 second delay, but also a medium delay of 1.5 seconds and a long delay of 2 seconds may be selected. It is preferred that the operator allow the treatment area to cool down just after treatment before the handpiece with the cooling tip is removed from treatment area. This may take a few hundred milliseconds.

When the system is in service mode an external unit may take over the control of the handpiece from the handpiece processor by taking control of the serial IIC bus. The handpiece processor checks whether an external computer is connected to the bus and if so control of the bus is transferred to the external computer. This may be useful when testing and adjusting the handpiece and when reprogramming the scanner.

Figure 7:
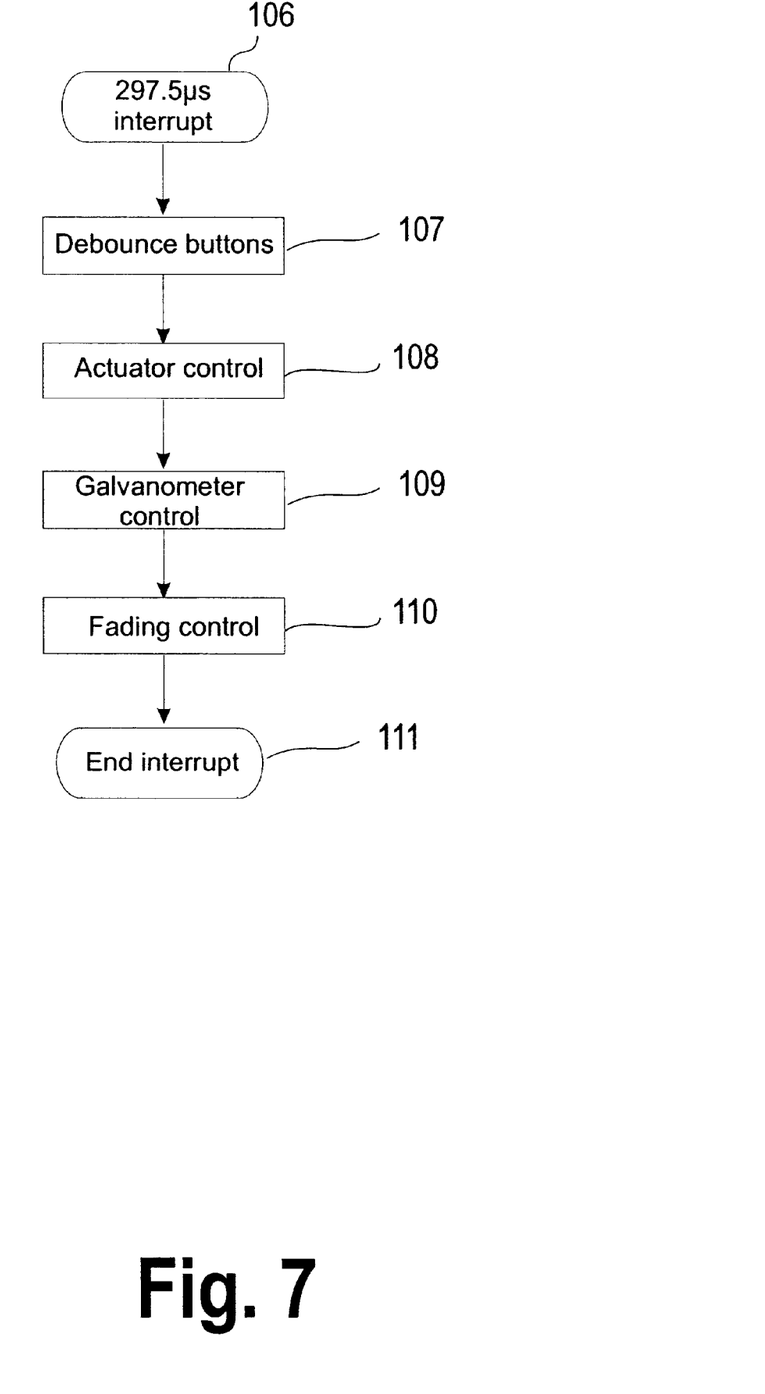
FIG. 7 shows a flow chart of the software controlling the scan parameters.

In FIG. 7 a flow chart illustrates a processor interrupt. This interrupt is executed every 297,5 microseconds and is set up during start up of the scanning sequence, and the set up information comprises information concerning the size, area, intensity, and velocity of the scan. At each interrupt, the processor checks whether one of the push buttons has been activated, and it reads in the table of the EEPROM the next position of the treatment beam and commands the moving means to the next position.

The first step 107 is debounce control of the buttons. Each time a signal from a push button is received, the signal is checked for 20 ms to avoid noise. The buttons are checked during start up and during guide scanning but during treatment scanning only the pedal is checked.

In step 108 the actuator is controlled according to the set up information and stepped as required. In step 109, the galvanometer is controlled and the current regulating the movements of the galvanometer is controlled. Further, in step 110 the fading or intensity of the beam is controlled according to the set up information. The interrupt is ended in step 111.

Figure 8:
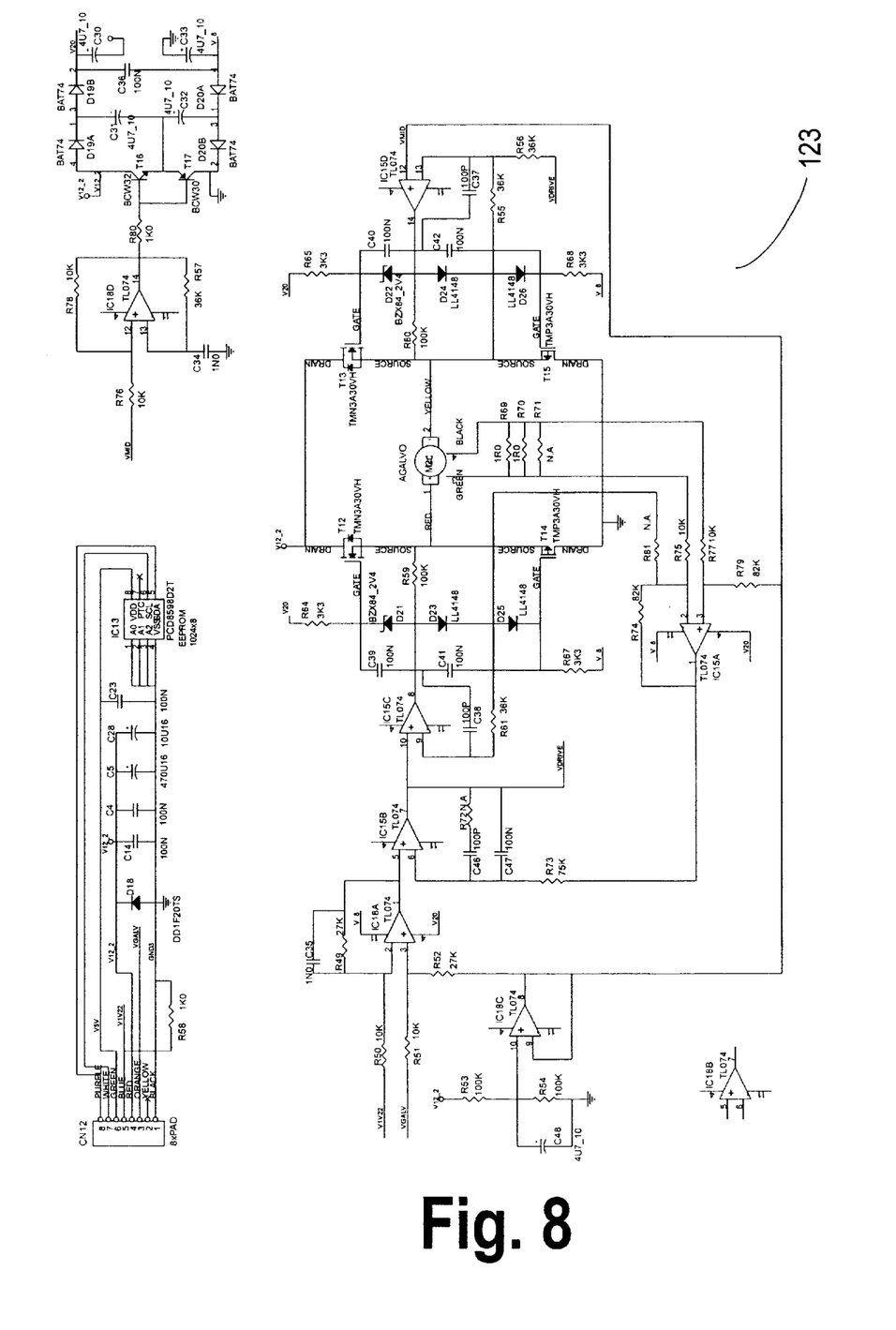
FIG. 8 shows an electric diagram of the galvanometer board.
Figure 9:
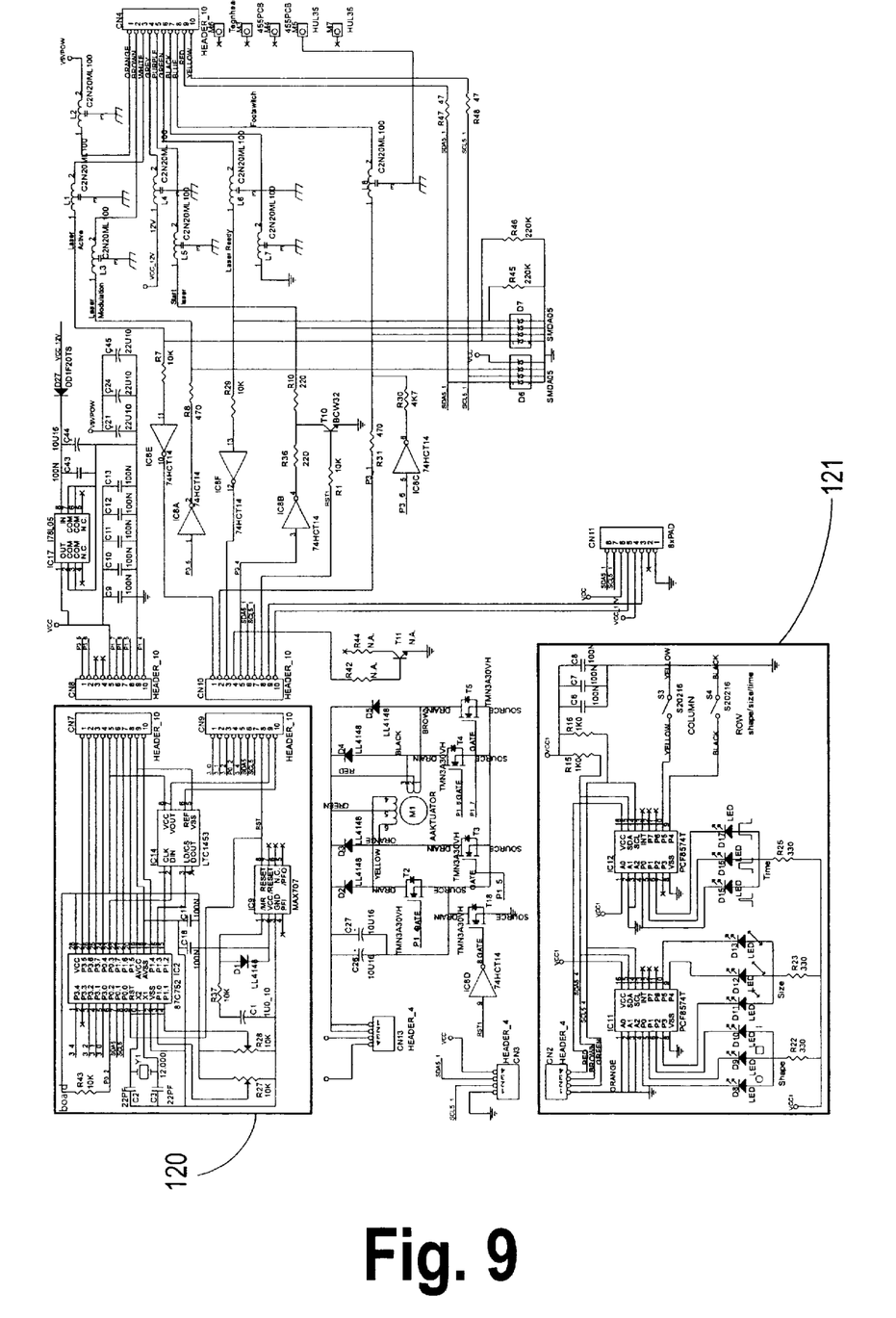
FIG. 9 shows an electric diagram of the electrical systems in the handpiece.

FIG. 8 and FIG. 9 show the electric diagrams depicting the operations of the processor IC2, e.g. a 87C752 from Phillips, at the controller board 120, the galvanometer M2 at the galvanometer board 123, the linear actuator M1, the push buttons and the light emitting diodes D8–D13 and D15–D17 at the display board 121 and the interconnections there between.

The processor IC2 is positioned in the handpiece and the voltage is supplied from the laser unit, e.g. a Uni-laser 450P main unit. The processor IC2 calculates the movements of the galvanometer M2 and of the linear actuator M1 from the selected treatment parameters (area, size and time). A IIC bus (not shown) is connecting the processor IC2 with the two interface integrated circuits IC11 and IC12, which may be PCF8574T from Philips.

When the handpiece is connected to the laser unit the operations of the laser unit is limited by the processor IC2 in the handpiece. The only parameters to be selected from the laser unit is the power, the pulses and the frequencies. The parameters chosen from the user interface, e.g. maximum scan time, intensity, scan size, and the scan shape, are stored in an EEPROM, e.g., a PCD8598D2T from Philips, where each parameter is stored in a record, which is readable from the processor IC2. In the EEPROM IC13 also off-set values for the actuator and the galvanometer are stored. As mentioned above, the parameters of the laser unit may also be selected from the handpiece by the selection of pre-stored programs.

The processor IC2 ensures that the scan is limited by the maximum treatment time chosen, and ensures that only one complete scan is performed when the pedal is activated. When the pedal is activated pin 8 at connector CN4 is high and the deflecting means are positioned to proper start positions by means of the connector CN11 to the galvanometer board BD3 and the connector CN3 to the actuator M1. The processor IC2 starts the laser unit without enabling the laser output IC8*b*. when the processor IC2 receives the signal 'Laser Active' from input IC8*e*, the processor IC2 starts to move the galvanometer M2 and the linear Actuator M1, and when these reach the proper positions the output power of the laser unit is enabled IC8*a*. During the enabling/disabling of the power at the laser unit the mirrors are still moved, output IC8*a*. When the selected treatment pattern is covered, the processor IC2 stops the laser unit, that is output IC8*b* is low. When the pedal is released the laser unit will still be ready for treatment, and by moving to an adjacent area and depressing the pedal a large area may be treated.

What is claimed is:

1. An apparatus for tissue treatment, comprising
a light emitter for emission of a continuous first light beam,
movable first deflecting means for deflection of the first light beam into a treating light beam,
an output for continuous emission of the treating light beam towards a target surface and illuminating a spot on the target surface,
first moving means for moving the first deflecting means, and
first deflecting control means for controlling the first moving means and being adapted to control the first moving means so that the treating light beam traverses a target surface area stepwise with steps that are greater than half the diameter of the spot and not larger than substantially the diameter of the spot, and in such a way that the spot treatment time at a specific treatment position is between 100 ms and 1 s.

2. An apparatus according to claim 1, wherein the step size is substantially equal to two thirds the diameter of the spot.

3. An apparatus according to claim 1, wherein the first deflecting control means are adapted to control the first moving means so that the treating light beam traverses a target surface area stepwise, sequentially line by line.

4. An apparatus according to claim 3, wherein the first deflecting control means are adapted to control the first moving means so that the treating light beam traverses a target surface area stepwise, sequentially line by line, without interlacing.

5. An apparatus according to claim 4, wherein the first deflecting control means are adapted to control the first moving means so that the treating light beam traverses a target surface area stepwise sequentially line by line in the same directions.

6. An apparatus according to claim 1, wherein the spot size ranges from 1 to 9 mm.

7. An apparatus according to claim 6, wherein the spot size is approximately 4 mm.

8. An apparatus according to claim 1, wherein the first deflecting means comprise a first mirror.

9. An apparatus according to claim 8, wherein the first deflecting means further comprise a second mirror.

10. An apparatus according to claim 1, further comprising light switching means for preventing emission of the treating light beam and light switching control means for controlling the light switching means.

11. An apparatus for tissue treatment according to claim 1, further comprising
    a handpiece comprising
        the first deflecting means,
        the first deflecting control means,
        the output, and
        an input connector for connection of a first beam-outlet end of a first optical fiber to the handpiece and for alignment of the first optical fiber with an axis of the handpiece so that a first light beam emitted from the first beam-outlet end is transmitted substantially along the axis,
    a light emitter for continuous emission of the first light beam, and
    the first optical fiber for transmission of the first light beam.

12. An apparatus according to claim 1, wherein the light emitter is adapted to emit light of a wavelength larger than 190 nm.

13. An apparatus according to claim 12, wherein the light emitter is adapted to emit light of a wavelength less than 3000 nm.

14. An apparatus according to claim 13, wherein the light emitter is adapted to emit light of a wavelength that is substantially equal to 810 nm.

15. An apparatus according to claim 1, wherein the light emitter is a laser that is adapted to emit laser light of an output power that is less than 250 W.

16. An apparatus according to claim 1, wherein the laser is adapted to emit light of an output power that is less than 150 W.

17. A handpiece for an apparatus for tissue treatment, comprising
    an input connector for connection of a first beam-outlet end of a first optical fiber to the handpiece and for alignment of the first optical fiber with an axis of the handpiece so that a first light beam emitted from the first beam-outlet end is transmitted substantially along the axis,
    movable first deflecting means for deflection of the first light beam into a treating light beam,
    an output for continuous emission of the treating light beam towards a target surface and illuminating a spot on the target surface,
    first moving means for moving the first deflecting means, and
    first deflecting control means for controlling the first moving means and being adapted to control the first moving means so that the treating light beam traverses a target surface area stepwise with steps that are greater than half the diameter of the spot and not larger than substantially the diameter of the spot, and in such a way that the spot treatment time at a specific treatment position is between 100 ms and 1 s.

18. A handpiece according to claim 17, wherein the step size is substantially equal to two thirds the diameter of the spot.

19. A handpiece according to claim 17, wherein the first deflecting control means are adapted to control the first moving means so that the treating light beam traverses a target surface area stepwise, sequentially line by line.

20. A handpiece according to claim 19, wherein the first deflecting control means are adapted to control the first moving means so that the treating light beam traverses a target surface area stepwise, sequentially line by line, without interlacing.

21. A handpiece according to claim 20, wherein the first deflecting control means are adapted to control the first moving means so that the treating light beam traverses a target surface area stepwise sequentially line by line in the same direction.

22. A handpiece according to claim 17, wherein the spot size ranges from 1 to 9 mm.

23. A handpiece according to claim 22, wherein the spot size is approximately 4 mm.

24. A handpiece according to claim 17, wherein the first deflecting means comprise a first mirror.

25. A handpiece according to claim 24, wherein the first deflecting means further comprise a second mirror.

26. A handpiece according to claim 17, further comprising light switching means for preventing emission of the treating light beam and light switching control means for controlling the light switching means.

27. A method of traversing a light beam across an area of a tissue for cosmetic treatment of the tissue, the method comprising the steps of
    continuously emitting the light beam towards the tissue area and illuminating a spot on the target surface,
    deflecting the light beam with movable deflecting means so that the tissue is traversed by the light beam stepwise with steps that are greater than half the diameter of the spot and not larger than substantially the diameter of the spot, and in such a way that the spot treatment time at a specific treatment position is between 100 ms and 1 s.

28. A method according to claim 27, wherein the step size is substantially equal to two thirds the diameter of the spot.

29. A method according to claim 27, wherein the target surface area is traversed stepwise, sequentially line by line.

30. A method according to claim 29, wherein the target surface area is traversed stepwise, sequentially line by line, without interlacing.

31. A method according to claim 30, wherein the target surface area is traversed stepwise, sequentially line by line in opposite directions.

32. A method according to claim 27, wherein the spot size ranges from 1 to 9 mm.

33. A method according to claim 32, wherein the spot size is approximately 4 mm.

* * * * *